United States Patent [19]

Thurman

[11] 4,151,353

[45] Apr. 24, 1979

[54] CARBAMOYL HALIDE COMPOSITIONS

[75] Inventor: Duane E. Thurman, Salinas, Calif.

[73] Assignee: Union Carbide Corporation, New York, N.Y.

[21] Appl. No.: 590,716

[22] Filed: Jun. 26, 1975

[51] Int. Cl.$^2$ ............... C07D 295/22; C07C 161/00
[52] U.S. Cl. ................................. 544/159; 544/58; 544/383; 548/337; 260/326.42; 260/465.4; 260/544 C; 546/153; 546/247
[58] Field of Search .......... 260/243 B, 268 S, 293.8 S, 260/283 S, 287 R, 295.8 S, 326.42, 465.4, 544 C; 544/58, 159, 383; 548/337

[56] References Cited

U.S. PATENT DOCUMENTS 3,699,163  10/1972  Kohn ........................... 260/544 C Primary Examiner—Natalie Trousof
Assistant Examiner—R. W. Ramsuer
Attorney, Agent, or Firm—Robert C. Brown

[57] ABSTRACT

N-(aminosulfenyl)carbamoyl halide compositions are useful intermediates in the production of carbamate compounds.

17 Claims, No Drawings

CARBAMOYL HALIDE COMPOSITIONS

This invention relates to a novel class of carbamoyl halide compositions and to their preparation.

The novel compositions of this invention are compounds corresponding to the following general formula:

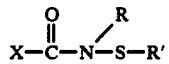

wherein: X may be fluorine or chlorine;

R may be hydrogen, lower alkyl, lower alkenyl, lower alkoxy or lower cycloalkyl either unsubstituted or substituted, except where R is hydrogen, with one or more chloro, bromo, fluoro, nitro or cyano substituents, or a combination thereof; or phenyl or lower phenylalkyl, either unsubstituted or substituted with one or more chloro, bromo, fluoro, nitro, cyano, lower alkyl, lower haloalkyl or lower alkoxy substituents, or a combination thereof;

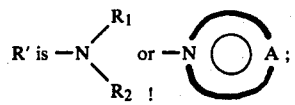

$R_1$ and $R_2$ are individually, hydrogen, alkyl, alkenyl, alkoxy, cycloalkyl, phenylalkyl, or phenyl, and which may be unsubstituted or, except in the case of hydrogen, substituted with one or more chloro, bromo, fluoro, nitro, cyano, lower alkyl, lower haloalkyl, or lower alkoxy substituents or a combination thereof; or a saturated or or unsaturated five or six membered heterocyclic radical in which there are one or two hetero atoms which may be oxygen, sulfur in any of its oxidation states, or nitrogen, including combinations thereof, all of which heterocyclic radicals may be unsubstituted or substituted with one or more chloro, bromo, fluoro, nitro, cyano, lower alkyl, lower haloalkyl, or lower alkoxy substituents or a combination thereof;

A is a divalent aliphatic chain which may be alkylene, alkenylene or an aliphatic chain which may include one or two hetero atoms of oxygen, sulfur or nitrogen or a combination thereof to form a five or six membered ring structure, which may be unsubstituted or substituted with one or more chloro, bromo, fluoro, nitro, cyano, lower alkyl, lower haloalkyl or lower alkoxy substituents or a combination thereof.

These compounds are valuable intermediates which are useful in the preparation of insecticidal compositions. Compositions of this invention react for example, with oxime compositions such as S-methyl-N-hydroxythiolacetimidate to form the corresponding N-(aminosulfenyl)carbamate compound which exhibits outstanding insecticidal properties. Compositions of this invention may also be reacted with other oxime compositions as more fully described in my co-pending U.S. patent application Ser. No. 590,463, filed concurrently herewith, to produce insecticidal and miticidal compositions.

The novel compositions of this invention can be prepared in a variety of ways. One preferred method of preparation is by the process shown in the following general reaction scheme:

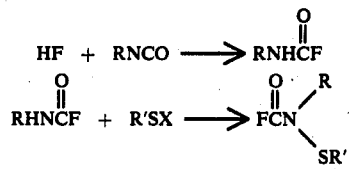

In the above equation and in those which follow below, R, R' and X are as defined above.

The reaction is conducted in the presence of an acid acceptor which may be a tertiary amine, such as trimethylamine or triethylamine; a heterocyclic base such as N-methylmorpholine, pyridine or quinoline or a metal hydroxylate such as sodium salt of phenol or an oxime.

This reaction also preferably conducted in the presence of an inert solvent such as methylene chloride, chloroform, dioxane, tetrahydrofuran, benzene, toluene, acetone, dimethoxyethane, dimethyl formaide, acetonitrile and the like.

Reaction-temperatures are not critical and may range from about −30° C. to about 75° C. Reaction pressures are also not critical in the conduct of this reaction although atmospheric or autogenous pressures are normally employed for reasons of convenience.

The N-aminosulfenyl reactants can be prepared by conventional methods as for example by the reaction of an appropriate secondary amine and sulfur dichloride or by chlorination of a bis-amine-disulfide as described in British Pat. No. 790,021, German Pat. No. 1,131,222 and U.S. Pat. No. 3,400,125.

Another method is as follows:

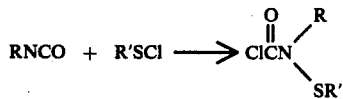

This reaction is preferably conducted in the presence of an inert solvent and at temperatures ranging from about −30° C. to about 100° C. The reaction is also preferably conducted in the presence of a Lewis acid.

A third method of producing these compositions is as follows:

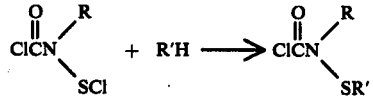

This reaction is also preferably conducted in the presence of an inert solvent and in the presence of an acid acceptor as described in reaction I. In this case a simple excess of the amine can be employed as an acid acceptor. The reaction can be carried out at temperatures ranging from about −30° C. to ambient.

The following examples are presented to more clearly illustrate the preparation of the novel compounds of this invention:

EXAMPLE I

Preparation of N-Methyl-N-(4-Morpholinosulfenyl) carbamoyl Fluoride

Anhydrous hydrogen fluoride (3.4 g, 0.17 mole) was added to 200 ml of toluene at −10° C. in a polyethylene reactor equipped with a stainless steel stirrer and thermocouple well, and a polyethylene dry ice condenser.

Methyl isocyanate (9.35 g, 0.17 mole) was then added dropwise; the temperature was maintained at −10° C. or less. Then, 26.3 g (0.17 mole) of freshly distilled 4-morpholinosulfenyl chloride was added to the mixture over a 20 minute period, and finally, 17.3 g (0.17 mole) triethylamine was added at −10° C. After the addition was completed the mixture was stirred and allowed to warm to room temperature for 30 minutes. It was filtered and the toluene filtrate was extracted twice with water and dried with magnesium sulfate. The toluene was removed in vacuo, and the residue was dissolved in boiling hexane, treated with decolorizing charcoal, filtered, and chilled. The resulting crystals were collected by suction filtration, and dried in vacuo to give 20 g. of N-methyl-N-(4-morpholinosulfenyl) carbamoyl fluoride m.p. 48°–50° C. (60.5 percent yield).

EXAMPLE II

Preparation of N-Isopropyl-N′(4-Morpholinosulfenyl)Carbamoyl Fluoride

To a mixture of 8.0 g (0.4 mole) of anhydrous hydrogen fluoride and 200 ml of methylene chloride in a polyethylene reactor fitted with a stainless steel stirrer and a thermocouple well was added 34.1 g (0.4 mole) of isopropyl isocyanate over a 0.5 hr. period at 0° C. The mixture was stirred for 1.5 hr. at 0.2° C., and then 4-morpholinosulfenyl chloride, prepared in situ by evaporating 14.5 g (0.2 mole) of chlorine into a slurry of 47.3 g (0.2 mole) of 4,4′-dithiobismorpholine in 100 ml of methylene chloride at −10° C., followed by stirring the mixture for 0.5 hr. at −10° C. to 0° C., and then sparging it with nitrogen for 0.5 hr. Triethylamine (40.4 g, 0.4 mole) was added over a 45 minute period at −10° C. The mixture was stirred for one hour and allowed to warm to room temperature in 1 hr. Water (200 ml) was added slowly while the mixture was stirred vigorously. The organic phase was washed with water, dried with anhydrous magnesium sulfate, filtered, and concentrated to give 53.0 g yellow oil, which upon recrystallization from hexane (chilled with dry-ice), yielded 24 g (27%) of N-isopropyl-N′(4-morpholinosulfenyl)carbamoyl fluoride m.p. 46°–48° C. and 1.6 g of N-(N′-isopropylcarbamoyl)morpholine as a by-product. The desired product crystallized out last.

Infrared: 5.65μ (C=O); 7.23 and 7.35μ (CHMC$_2$); 7.85μ (C—F); 9.0μ (C—O—C)

NMR: (CDCl$_3$)—δ1.25 and δ1.37 (two doublets, J=1.5 Hz, 6H, —CHMe$_2$); δ3.25 and "3.72 (two multiplets, 8H, morpholine ring protons); δ4.14 (m, J=7 Hz, 1H, CHMe$_2$)

EXAMPLE III

Preparation of N-Methyl-N(1-Piperidinosulfenyl) Carbamoyl Fluoride

Anhydrous hydrogen fluoride (10.0 g, 0.5 mole) was added to 400 ml of methylene chloride at −10° C. in a polyethylene reactor fitted with a stainless steel stirrer and a thermocouple well. To this solution was added 28.6 g (0.5 mole) of methyl isocyanate in 15 min. at −10° C. The mixture was stirred for 20 min. To the mixture was then added 1-piperidinosulfenyl chloride, prepared in situ by evaporating 18.0 g (0.25 mole) of chlorine into a slurry of 58.1 g 10.25 mole) of 1,1′-dithiobispiperidine in 150 ml of methylene chloride at −10° C., followed by stirring the mixture for 0.5 hr. and then sparging it with nitrogen for 20 min. to remove the excess chlorine. Triethylamine (50.6 g, 0.5 mole) was added dropwise to the above mixture at −10° C. The mixture was stirred for 0.5 hr. and then allowed to warm to 0° C. After the addition of 250 ml of water, the methylene chloride layer was agitated thoroughly and was washed once again with 250 ml of water, dried over anhydrous magnesium sulfate, filtered and concentrated to give 61 g reddish liquid residue. Distillation of the residue at 74°–76° C./0.38 mm yielded 44.2 g of N-methyl-N-(1-piperidinosulfenyl carbamoyl fluoride (46%) as an amber liquid.

Infrared: 3.5μ (N—CH$_2$); 5.6μ (C=O); 7.05μ (N—CH$_3$); 7.78μ (C—F)

NMR CDCl$_3$): α1.52 (m, 6H, —CH$_2$— β and γ to N); α3.28 (m, 4H, —CH$_2$— γ to N); α3.35 (α J=1 Hz, 3H, N-CH$_3$)

Anal. Calculated for CH$_{13}$FN$_2$OS: C, 43.73; H, 6.81; N, 14.57 Found: C, 43.57; H, 6.50; N, 14.44

EXAMPLE IV

Preparation of N-Methyl-N-(4-Morpholinosulfenyl)carbamoyl Fluoride

Sulfur dichloride (61.8 g, 0.6 mole) was charged to a 2-liter reaction flask containing 700 ml of methylene chloride at −15° C. A mixture of 52.7 g (0.6 mole) of morpholine and 60.6 g (0.6 mole) of triethylamine was then added dropwise with stirring over a 1.5-hour period. The reaction was held at −10° C. during the addition. After the addition was completed, the mixture was stirred at −10° to −15° C. for 0.5 hour, and then was used in a reaction (below) with methylcarbamoyl fluoride without filtration of the precipitated amine salts.

While the above reaction was in progress, 700 ml of methylene chloride was charged to a polyethylene reactor and cooled to −15° C. The reactor was equipped with a stainless steel thermocouple well and stirrer, and a Teflon addition tube fitted to a dropping funnel and nitrogen inlet line. A dry-ice tray was fitted around the Teflon tube so as to act as a cold finger condenser. Liquid hydrogen fluoride (11 g, 0.55 mole) was weighed out into a tared cold trap, and then was poured rapidly into the reactor. Methyl isocyanate (31.4 g, 0.55 mole) was then added dropwise while the temperature was maintained at −10° C. The mixture of 4-morpholinosulfenyl chloride and triethylamine hydrochloride prepared above was then added to the reactor rapidly by pouring it in through the Teflon sidearm. The mixture was stirred and 55.7 g of triethylamine was added over a 30-minute period. The mixture was then warmed to +10° C. and was extracted with water and then sodium bicarbonate solution. The methylene chloride solution was dried with MgSO$_4$, and was concentrated in vacuo to give a brown oil which solidified when triturated with n-hexane. The solids were collected by filtration and dried in vacuo to give 75 g (64 percent yield) of crude N-methyl-N-(4-morpholinosulfenyl) carbamoyl fluoride.

EXAMPLE V

Preparation of N-Methyl-N-(4-Morpholinosulfenyl) carbamoyl Fluoride

Sulfur monochloride (135.1 g, 1.0 mole) was added dropwise at −15° C. to a solution of 174.2 g (2.0 mole) of morpholine and 202.4 g (2.0 mole) of triethylamine in 1700 ml of dry methylene chloride. External cooling was used to hold the reaction temperature at −15° C.

during the addition. The mixture was stirred 0.5 hour at −15° C. and then was warmed to room temperature and was extracted twice with water (500 ml). The organic solution of 4,4'-bismorpholinodisulfide was then dried (MgSO₄), filtered, charged to a 3-liter reactor, and was cooled to −15° C. for chlorination.

Chlorine (71 g, 1 mole) was evaporated from a tared cold trap into the stirred solution of 4,4'-bismorpholinodisulfide. The temperature was maintained at −10° C. to −15° C. during the addition. After the addition was completed, a nitrogen sparge was used to expel any excess chlorine. The resulting solution of 4-morpholinosulfenyl chloride was then used immediately in a reaction with methylcarbamoyl fluoride, prepared via: Anhydrous hydrogen fluoride (40 g) was added to 500 ml of methylene chloride at −10° C. in a polyethylene reactor. Methylisocyanate (114 g) was then added slowly at −10° C. The mixture was stirred for 1 hour at 0° C., and then recooled to −10° C. The methylene chloride solution of 4-morpholinosulfenyl chloride, prepared as described above, was then added rapidly. The mixture was stirred at 0° C. for 0.5 hour, and then 202 g of triethylamine was added dropwise. This mixture was stirred at 0° C. for 0.5 hour, and then was extracted three times with water, dried (MgSO₄), and concentrated in vacuo. The residue was dissolved in boiling benzene, treated with decolorizing charcoal, gravity filtered, and concentrated. Recrystallization from hexane, then afforded 186 g of N-methyl-N-(4-morpholinosulfenyl)carbamoyl fluoride (46.7 percent yield based on morpholine).

EXAMPLE VI

Preparation of N-Methyl-N-(Dimethylaminosulfenyl)carbamoyl Fluoride

Anhydrous hydrogen fluoride (14.2 g., 0.71 mole) was added to 400 ml toluene at −50° C. and this solution was then charged to a polyethylene reactor. Methyl isocyanate (41.0 g, 0.71 mole) was then added dropwise over a 15-minute period. The mixture was stirred and warmed to 0° C. for 1 hr. N,N-Dimethylaminosulfenyl chloride (80.0 g, 0.71 mole, freshly distilled) was then added dropwise over a 5 minute period. The reaction mixture was allowed to warm to 10° C., and then 74 g of triethylamine was added dropwise. External cooling was used to maintain the temperature at 5°–10° C. After the addition was completed the mixture was stirred at ambient temperature for 1 hr., filtered, and the organic filtrate was water washed. The toluene solution was dried (MgSO₄), concentrated in vacuo, and the residue was vacuum distilled to give 55 g of N-methyl-N-(dimethylaminosulfenyl)carbamoyl fluoride, b.p. 55°–57°, C./5.0 mm (50.9 percent yield).

EXAMPLE VII

Preparation of N-Methyl-N-(Diethylaminosulfenyl) carbamoyl Fluoride

Anhydrous hydrogen fluoride (3.0 g, 0.15 mole) was added to 150 ml of methylene chloride at −10° C. Then 8.6 g of methylisocyanate was added, followed by 20.9 g (0.15 mole) of N,N-diethylaminosulfenyl chloride at 0° C. Triethylamine (15.2 g) was then added at 0° C. over a 15-minute period, and the mixture was stirred at +5° C. for 1 hour. The mixture was then extracted with water (100 ml), saturated sodium bicarbonate solution, and water again. After drying (MgSO₄), the solvent was removed in vacuo, and the crude residue was vacuum distilled to give 17 g of N-methyl-N-(diethylaminosulfenyl carbamoyl fluoride, b.p. 57° C./0.8 mm (62.9 percent yield).

Anal. Calc'd. for $C_6H_{13}FN_2O_5$: C, 39.98; H, 7.27; N, 15.54. Found: C, 39.82; H, 6.83; N, 14.95.

EXAMPLE VIII

Preparation of N-Phenyl-N-(4-Morpholinosulfenyl) carbamoyl Fluoride,

Anhydrous hydrogen fluoride (4.0 g) was added to methylene chloride (150 ml) at −10° C. in a polyethylene reactor. Phenyl isocyanate (23.8 g, 0.2 mole) was then added dropwise over a 20 minute period. This mixture was stirred at 5° C. for 1 hour, and then a solution of 30.6 g (0.2 mole) of 4-morpholinosulfenyl chloride in 75 ml of methylene chloride was added rapidly. Triethylamine (20.2 g) was then added slowly at −10° C. The mixture was then stirred and warmed to 0° C. for 1 hr., water extracted twice, dried (MgSO₄), and concentrated in vacuo. The resulting dark residue was vacuum distilled to remove volatile impurities, and then the kettle residue was extracted with hot hexane. The hexane solution upon cooling deposited 6 g of N-phenyl-N-(4-morpholinosulfenyl)carbamoyl fluoride, m.p. 71°–72° C., (11 percent yield).

Infrared: 5.6μ, C=O.

NMR: CDCl₃: multiplets at δ3.25 and 3.66 ppm (4H each); single at δ7.36 ppm (5H).

Anal. Calc'd. for $C_{11}H_{13}FN_2O_2S$: C, 51.55; H, 5.11; N, 10.93. Found: C, 52.27; H, 5.41; N, 10.94.

Illustrative of the new compositions of matter which can be prepared by the above processes are the following:

N-methyl-N-(dimethylaminosulfenyl) carbamoyl fluoride

N-methyl-N-(diethylaminosulfenyl) carbamoyl fluoride

N-methyl-N-(diiospropylaminosulfenyl) carbamoyl fluoride

N-methyl-N-(di-n-butylaminosulfenyl) carbamoyl fluoride

N-methyl-N-(diisobutylaminosulfenyl) carbamoyl fluoride

N-methyl-N-(di-sec-butylaminosulfenyl) carbamoyl fluoride

N-methyl-N-(di-n-pentylaminosulfenyl) carbamoyl fluoride

N-methyl-N-(di-n-octylaminosulfenyl) carbamoyl fluoride

N-methyl-N-(methylethylaminosulfenyl) carbamoyl fluoride

N-methyl-N-(methylbutylaminosulfenyl) carbamoyl fluoride

N-methyl-N-(methylcyclohexylaminosulfenyl) carbamoyl fluoride

N-methyl-N-dicyclohexylaminosulfenyl) carbamoyl fluoride

N-methyl-N-(methylcyanomethylaminosulfenyl) carbamoyl fluoride

N-methyl-N-(methylbenzylaminosulfenyl) carbamoyl fluoride

N-methyl-N-(dibenzylaminosulfenyl) carbamoyl fluoride

N-methyl-N-(methylphenylaminosulfenyl) carbamoyl fluoride

N-methyl-N-[methyl(4-chlorophenyl) aminosulfenyl] carbamoyl fluoride

N-methyl-N-(methoxymethylaminosulfenyl) carbamoyl fluoride
N-methyl-N-(methyldodecylaminosulfenyl) carbamoyl fluoride
N-methyl-N-(1-pyrrolidinosulfenyl) carbamoyl fluoride
N-methyl-N-(1-piperidinosulfenyl) carbamoyl fluoride
N-methyl-N-(4-morpholinosulfenyl) carbamoyl fluoride
N-methyl-N-(4-methyl-1-piperazinosulfenyl) carbamoyl fluoride
N-methyl-N-(4-thiomorpholinosulfenyl) carbamoyl fluoride
N-methyl-N-[1-(4-methylpiperidino) sulfenyl] carbamoyl fluoride
N-methyl-N-(1-imidazolylsulfenyl) carbamoyl fluoride
N-methyl-N-(1-1,2,3,4-tetrahydroquinolinosulfenyl) carbamoyl fluoride
N-ethyl-N-(dimethylaminosulfenyl) carbamoyl fluoride
N-isopropyl-N-(4-morpholinosulfenyl) carbamoyl fluoride
N-phenyl-N-(4-morpholinosulfenyl) carbamoyl fluoride
N-methyl-N-(dimethylaminosulfenyl) carbamoyl chloride
N-methyl-N-(4-morpholinosulfenyl) carbamoyl chloride
N-methyl-N-(diisopropylaminosulfenyl) carbamoyl chloride
N-allyl-N-(4-morpholinosulfenyl) carbamoyl fluoride
N-methoxy-N-(4-morpholinosulfenyl) carbamoyl fluoride
N-cyclohexyl-N-(4-morpholinosulfenyl) carbamoyl fluoride
N-cyclopentyl-N-(4-morpholinosulfenyl) carbamoyl fluoride
N-benzyl-N-(4-morpholinosulfenyl) carbamoyl fluoride
N-chloromethyl-N-(4-morpholinosulfenyl) carbamoyl fluoride
N-cyanomethyl-N-(4-morpholinosulfenyl) carbamoyl fluoride
N-(4-bromophenyl)-N-(4-morpholinosulfenyl) carbamoyl fluoride
N-(4-fluorophenyl)-N-(4-morpholinosulfenyl) carbamoyl fluoride
N-(4-nitrobenzyl)-N-(4-morpholinosulfenyl) carbamoyl fluoride
N-(2-trifluoromethyl-4-chlorophenyl)-N-(4-morpholinosulfenyl) carbamoyl fluoride
N-(4-methylphenyl)-N-(4-morpholinosulfenyl) carbamoyl fluoride
N-methyl-N-(3-tetrahydrothiophenylsulfenyl) carbamoyl fluoride
N-methyl-N-(3-tetrahydrothiophenyl-1-oxide sulfenyl) carbamoyl fluoride
N-methyl-N-(3-tetrahydrothiophenyl-1,1-dioxide sulfenyl)-carbamoyl fluoride
N-methyl-N-(methylaminosulfenyl) carbamoyl fluoride
N-methyl-N-(4-bromophenylmethylaminosulfenyl) carbamoyl fluoride
N-methyl-N-(chloromethylmethylaminosulfenyl) carbamoyl fluoride
N-methyl-N-(fluoromethylmethylaminosulfenyl) carbamoyl fluoride
N-methyl-N-(4-nitrophenylmethylsulfenyl) carbamoyl fluoride
N-methyl-N-(2-trifluoromethylphenylmethylsulfenyl) carbamoyl fluoride
N-methyl-N-(4-methylphenylmethylsulfenyl) carbamoyl fluoride
N-methyl-N-(allylmethylsulfenyl) carbamoyl fluoride Physical data of representative new compounds according to this invention are set forth in Table I below.

TABLE 1

PHYSICAL DATA FOR NOVEL N-AMINOSULFENYL) CARBAMOYL FLUORIDES $$\text{FCN}-\overset{\overset{O}{\|}}{\underset{}{S}}-\overset{R}{R^1}$$

| Ex. No. | R | R$^1$ | M.P. °C. (B.P. °C./mm) | Empirical Formula | Calc'd %C | %H | %N | Found %C | %H | %N |
|---|---|---|---|---|---|---|---|---|---|---|
| 1 | CH$_3$ | —N⟨O⟩ (morpholino) | 49–50 | C$_6$H$_{11}$FN$_2$O$_2$S | 37.10 | 5.71 | 14.42 | 36.44 | 5.57 | 14.02 |
| 2 | CH$_3$ | —N⟨ ⟩ (piperidino) | (74/0.38) | C$_7$H$_{13}$FN$_2$OS | 43.73 | 6.81 | 14.57 | 43.57 | 6.50 | 14.44 |
| 3 | CH$_3$ | —N(CH$_3$)$_2$ | (55-7/5.0) | C$_4$H$_9$FN$_2$OS | 31.6 | 6.0 | 18.4 | 32.5 | 6.0 | 18.1 |
| 4 | CH$_3$ | —N(C$_2$H$_5$)$_2$ | (59/0.79) | C$_6$H$_{13}$FN$_2$OS | 39.98 | 7.27 | 15.54 | 39.82 | 6.83 | 14.95 |
| 5 | CH$_3$ | —N(C$_4$H$_9$)$_2$ | (84/0.15) | C$_{10}$H$_{21}$FN$_2$OS | 50.81 | 8.95 | 11.85 | 51.16 | 8.72 | 11.86 |
| 6 | —CH(CH$_3$)$_2$ | —N⟨O⟩ (morpholino) | 46–48 | C$_8$H$_{15}$FN$_2$O$_2$S | 43.23 | 6.80 | 12.60 | 43.41 | 6.72 | 12.69 |
| 7 | —C$_6$H$_5$ | —N⟨O⟩ (morpholino) | 71–2 | C$_{11}$H$_{13}$FN$_2$O$_2$S | 51.55 | 5.11 | 10.95 | 52.27 | 5.41 | 10.93 |
| 8 | CH$_3$ | —N[CH(CH$_3$)$_2$]$_2$ | (60/0.15) | C$_8$H$_{17}$FN$_2$OS | 46.13 | 8.22 | 13.45 | 45.81 | 7.81 | 13.29 |
| 9 | CH$_3$ | —N(C$_2$H$_5$)(C$_4$H$_9$) | (67/0.2) | C$_8$H$_{17}$FN$_2$OS | | | | | | |

What is claimed is:
1. Compounds of the formula:

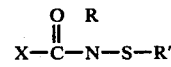

wherein:

X is fluorine or chlorine;

R may be hydrogen, lower alkyl, lower alkenyl, lower alkoxy or lower cycloalkyl either unsubstituted or, except where R is hydrogen, substituted with one or more chloro, bromo, fluoro, nitro or cyano substituents or a combination thereof or phenyl or lower phenyl alkyl, either unsubstituted or substituted with one or more chloro, bromo, fluoro, nitro, cyano, lower alkyl, lower haloalkyl or lower alkoxy substituents or a combination thereof;

$$R' \text{ is } -N\begin{array}{c}R_1\\ \\R_2\end{array} \text{ or } -N\bigcirc A;$$

$R_1$ and $R_2$ are individually, hydrogen, alkyl, alkenyl, alkoxy, cycloalkyl, phenylalkyl, phenyl, which may be unsubstituted or substituted, except in the case of hydrogen, with one or more chloro, bromo, fluoro, nitro, cyano, lower alkyl, lower haloalkyl, or lower alkoxy substituents or a combination thereof; or a saturated or unsaturated five or six membered heterocyclic radical in which there are one or two hetero atoms which may be oxygen, sulfur in all of its oxidation states or nitrogen including combinations thereof, all of which heterocyclic radicals may be unsubstituted or substituted with one or more chloro, bromo, fluoro, nitro, cyano, lower alkyl, lower haloalkyl, or lower alkoxy substituents or a combination thereof;

A is a divalent aliphatic chain which may be alkylene, alkenylene or an aliphatic chain which may include one or two hetero atoms of oxygen, sulfur or nitrogen or a combination thereof to form a five or six membered ring structure which may be unsubstituted or substituted with one or more chloro, bromo, fluoro, nitro, cyano, lower alkyl, lower haloalkyl or lower alkoxy substituents or a combination thereof.

2. A compound according to claim 1 wherein X is fluorine.

3. A compound according to claim 1 wherein X is chlorine.

4. A compound according to claim 1 wherein R is lower alkyl having from 1 to 8 carbon atoms.

5. A compound according to claim 1 wherein R is phenyl.

6. A compound according to claim 1 wherein R' is $$-N\begin{array}{c}R_1\\ \\R_2\end{array}$$

7. A compound according to claim 1 wherein R' is a dilower alkyl amino group.

8. A compound according to claim 1 wherein R' is $$-N\bigcirc A.$$

9. A compound of the formula:

$$\begin{array}{cc}O & R\\ \| & |\\X-C-N-S-R'\end{array}$$

wherein:

X is fluorine or chlorine;

R is hydrogen, lower alkyl, lower alkoxy, lower alkenyl or lower cycloalkyl which may be unsubstituted or, except in the case of hydrogen substituted with one or more bromo, chloro, fluoro, or nitro substituents or a combination thereof;

R' is a five or six membered ring structure which includes one or two hetero atoms of nitrogen which may be unsubstituted or substituted with one or more chloro, bromo, fluoro, nitro, lower alkyl, lower haloalkyl or lower alkoxy substituents or a combination thereof.

10. A compound of the formula:

$$\begin{array}{cc}O & R\\ \| & |\\X-C-N-S-R'\end{array}$$

wherein:

X is fluorine or chlorine;

R is hydrogen, lower alkyl, lower alkoxy, lower alkenyl or lower cycloalkyl which may be unsubstituted or, except in the case of hydrogen, substituted with one or more bromo, chloro, fluoro, or nitro substituents or a combination thereof;

R' is morpholino, which may be unsubstituted or substituted with one or more chloro, bromo, fluoro, nitro, lower alkyl, lower haloalkyl or lower alkoxy substituents or a combination thereof.

11. A compound according to claim 10 wherein R is lower alkyl having from 1 to 8 carbon atoms.

12. A compound of the formula:

$$\begin{array}{cc}O & R\\ \| & |\\X-C-N-S-R'\end{array}$$

wherein:

X is chlorine or fluorine;

R is hydrogen, lower alkyl, lower alkenyl, lower alkoxy or lower cycloalkyl either unsubstituted or substituted, except where R is hydrogen, with one or more chloro, bromo, fluoro, nitro or cyano substituents, or a combination thereof; or phenyl or lower phenylalkyl, either unsubstituted or substituted with one or more chloro, bromo, fluoro, nitro, cyano, lower alkyl, lower haloalkyl or lower alkoxy substituents or a combination thereof;

R' is —N A, wherein, A is a divalent alkylene chain completing a morpholino, piperidino, pyrrolidino, piperazino or thiomorpholino ring structure.

13. A compound according to claim 10 wherein R' is a piperidine group.

14. A compound according to claim 10 wherein R' is a morpholine group.

15. N-methyl-N-(dimethylamimosulfenyl) carbamoyl fluoride.

16. N-methyl-N-(diisopropylaminosulfenyl) carbamoyl fluoride.

17. N-methyl-N-(4-morpholinosulfenyl) carbamoyl fluoride.

* * * * *

UNITED STATES PATENT AND TRADEMARK OFFICE
CERTIFICATE OF CORRECTION

PATENT NO. : 4,151,353
DATED : 4/24/79
INVENTOR(S) : D. E. Thurman

It is certified that error appears in the above-identified patent and that said Letters Patent are hereby corrected as shown below:

Column 1, lines 25-28, page 2 line 17 in specification, and column 9, lines 13-16, the formula reads as follows: (each occurrence):

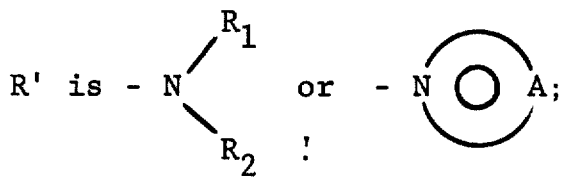

the formula should read:

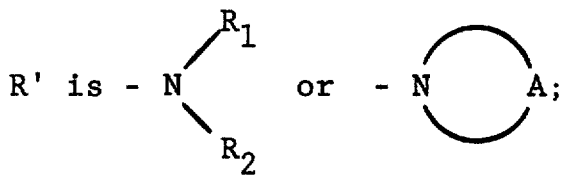

UNITED STATES PATENT AND TRADEMARK OFFICE
CERTIFICATE OF CORRECTION

PATENT NO. : 4,151,353

DATED : 4/24/79

INVENTOR(S) : D. E. Thurman

It is certified that error appears in the above-identified patent and that said Letters Patent are hereby corrected as shown below:

Column 9, lines 61-64, the formula reads as follows: (Claim 8 of specification):

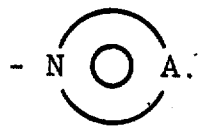

The formula should read:

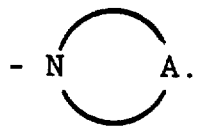

Signed and Sealed this

Twenty-fifth Day of March 1980

[SEAL]

Attest:

SIDNEY A. DIAMOND

Attesting Officer — Commissioner of Patents and Trademarks